United States Patent [19]
Klomhaus

[11] Patent Number: 5,685,301
[45] Date of Patent: Nov. 11, 1997

[54] APPARATUS FOR PRECISE DETERMINATION OF OPERATING CHARACTERISTICS OF OPTICAL DEVICES CONTAINED IN A MONITORING PROBE

[75] Inventor: Jill Taylor Klomhaus, Boulder, Colo.

[73] Assignee: Ohmeda Inc., Liberty Corner, N.J.

[21] Appl. No.: 491,437

[22] Filed: Jun. 16, 1995

[51] Int. Cl.$^6$ ........................................ A61B 5/00
[52] U.S. Cl. ........................................ 128/633
[58] Field of Search .................... 128/633, 634, 128/664, 665; 356/39–41

[56] References Cited

U.S. PATENT DOCUMENTS

| | | | |
|---|---|---|---|
| 5,204,532 | 4/1993 | Rosenthal | 128/633 X |
| 5,267,562 | 12/1993 | Ukawa et al. | 128/633 |
| 5,297,548 | 3/1994 | Pologe | 128/633 |
| 5,313,552 | 5/1994 | Lindsay . | |
| 5,357,953 | 10/1994 | Merrick et al. | 128/665 X |
| 5,421,329 | 6/1995 | Casciani et al. | 128/633 |

FOREIGN PATENT DOCUMENTS

0329196  4/1994  European Pat. Off. .

Primary Examiner—Jennifer Bahr
Assistant Examiner—Samuel Gilbert
Attorney, Agent, or Firm—William A. Schoneman; Roger M. Rathbun; Salvatore P. Pace

[57] ABSTRACT

The apparatus of the present invention characterizes the operating characteristics of a medical monitoring probe in a more comprehensive and accurate manner than is heretofore known in the prior art. This apparatus not only identifies the present value of a plurality of operating characteristics of the optical components contained in the probe, but also computes the interrelationship therebetween to produce a composite probe indicia that substantially defines the net operating characteristics of the probe, including the interrelation of the various interactive and/or cumulative effects. This composite probe indicia represents either a number or a graphical representation of probe operating characteristics that can be used directly by the processor contained within the monitoring system to perform the required computations.

18 Claims, 7 Drawing Sheets

APPARATUS FOR PRECISE DETERMINATION OF OPERATING CHARACTERISTICS OF OPTICAL DEVICES CONTAINED IN A MONITORING PROBE

FIELD OF THE INVENTION

This invention relates to photoplethysmographic systems that make use of a probe which generates radiation in the visible and infrared regions to illuminate a site on a patient that is rich in arterial blood flow and to apparatus which precisely identifies the operating characteristics of the optical apparatus in the probe in order to improve the accuracy of the measurements made by the photoplethysmographic system.

PROBLEM

It is a problem in the field of monitoring instruments to produce measurements of high accuracy when using nonideal commercially available probe components to measure a variable of small magnitude which is extant in a noisy environment. One example of such a monitoring instrument is a photoplethysmographic system that measures the concentration of analytes contained in the arterial blood of a patient by monitoring the differential change in the amount of light that is absorbed by these analytes when perfused tissue of the subject is illuminated with light of predetermined wavelengths. It is well known, according to Beer's law, that the absorption of light of predetermined wavelength is a function of the concentration of the analyte in the arterial blood. The accuracy of this determination can be compromised by variations in the wavelength of operation and the basic broad band nature of the light emitting diodes, since there is a significantly varying non-linear relationship between the absorbance characteristic of a monitored analyte and the wavelengths of light with which it is illuminated.

Existing photoplethysmographic systems simply characterize each LED operating wavelength by a wavelength index, which comprises a single one of: the measured peak wavelength, or wavelength center of mass, or wavelength range. This wavelength index is relayed to the processor contained within the photoplethysmographic system by use of a "binning resistor" located in the probe, whose impedance value is an indication of a one of these operating wavelengths, with the correspondence between impedance and the identified wavelengths being stored in a lookup table in the processor's memory. In operation, the magnitude of the error caused by the discrepancy between the actual operating characteristics of the light emitting diodes and the nominal value assigned thereto is partly determined by the non-linear absorption characteristic of the measured analyte as a function of wavelength. In practice, the granularity of the choices available for nominal wavelength of the light emitting diodes is coarse, with only a few most commonly found wavelength pairs being suitable for use. Therefore, any light emitting diode that, when tested, does not conform to these few selected wavelengths must be discarded and the labor and materials invested in performing this test is thereby wasted.

In addition to the lack of granularity in the definition of available wavelengths, no attempt is made to quantify or characterize the additional operating characteristics of the light emitting diodes or the remaining optical elements contained in the probe. Two LEDs can have the same wavelength index yet can vary in bandwidth and waveshape (for example: skew, symmetry, notched peaks, etc.). Furthermore, the optical detectors contained in the probe have a nonlinear response as a function of wavelength. These neglected factors can also effect the accuracy of the resultant measurements and can have a greater or lesser impact on the accuracy of the measurements as a function of whether the various factors have an additive or cancelling effect on the measurements that are taken. Due to the complexity involved in attempting to characterize these various factors in any meaningful way, the photoplethysmographic systems of the prior art have totally ignored these factors and simply provide a rudimentary notation of nominal light emitting diode wavelengths by use of selected binning resistor values.

SOLUTION

The above described problems are solved and a technical advance achieved in the field by the apparatus of the present invention which determines the operating characteristics of the apparatus contained in a medical monitoring probe in a more comprehensive and accurate manner than is heretofore known in the prior art. In addition, more light emitting diodes are thereby accommodated, which results in fewer parts being discarded and less testing labor lost.

This system not only identifies a number of operating characteristics of the light emitting diodes but also computes the interrelationship between these characteristics and other probe operating characteristics to produce a composite probe indicia which substantially defines the net operating characteristics of the probe, including the interrelation of the various interactive and/or cumulative effects. One implementation of the composite probe indicia comprises an effective optical extinction value that can be used directly by the processor contained within the photoplethysmographic system to select the most accurate one of a family of operating characteristic curves to perform the required computations. In an alternative embodiment, the composite probe indicia can be represented in a graphical format as a pilot of composite probe transfer characteristic as a function of analyte concentration.

There are a plurality of factors in photoplethysmographic systems that are a function of the wavelength used to illuminate the perfused monitoring site on a patient. These factors can be combined by computing a scaler or dot product of the various characteristic curves of, for example, the light output characteristic of the light emitting devices, the response curve of the light detector, and the extinction coefficient for a particular analyte. The light output curve for a light emitting device is a representation of the intensity of light produced by this device or the continuum of wavelengths of light that are of interest. This light output curve is typically asymmetrically bell-shaped with long tails, which tails can significantly effect the performance of the photoplethysmographic system if they are ignored in the computation process. The extinction curve is a representation of the light absorptivity of the analyte of interest at the spectrum of wavelengths that correspond to the light that impinges on the perfused tissue. The extinction curve is non-linear and is scientifically determined. The response curve of the light detector is a mapping of the sensitivity or responsiveness of the light detector device to wavelengths that fall within the spectrum of interest. When graphically represented, these three characteristic curves illustrate that the net effect of all of these factors for variations in wavelength can vary significantly.

The system of the present invention calculates a mathematical representation of the composite effect of these various factors to provide a simple yet far more accurate representation of the probe characteristics than that which is simply nominal wavelength. One method of performing this calculation is to mathematically combine the value of each of these characteristics at selected wavelengths over the range of wavelengths of interest to thereby produce a composite value for each analyte of interest, which together are used to produce a unique composite characteristic curve for the probe. This thereby enables the photoplethysmographic apparatus to perform its computations using what is essentially a transfer characteristic of the probe. This transfer characteristic can be stored in its entirety in the probe memory or, if there are substantial pattern similarities among probes, can be represented by a pointer value which can be translated by the equipment to one of a plurality of predefined transfer characteristic curves stored in the processor memory. In either case, the computations performed by the photoplethysmographic apparatus using a transfer characteristic curve that presents a composite image of the unique probe rather than one based on a simplistic nominal wavelength value produces results of much higher accuracy than existing computational methods.

DETAILED DESCRIPTION

Figure 1:
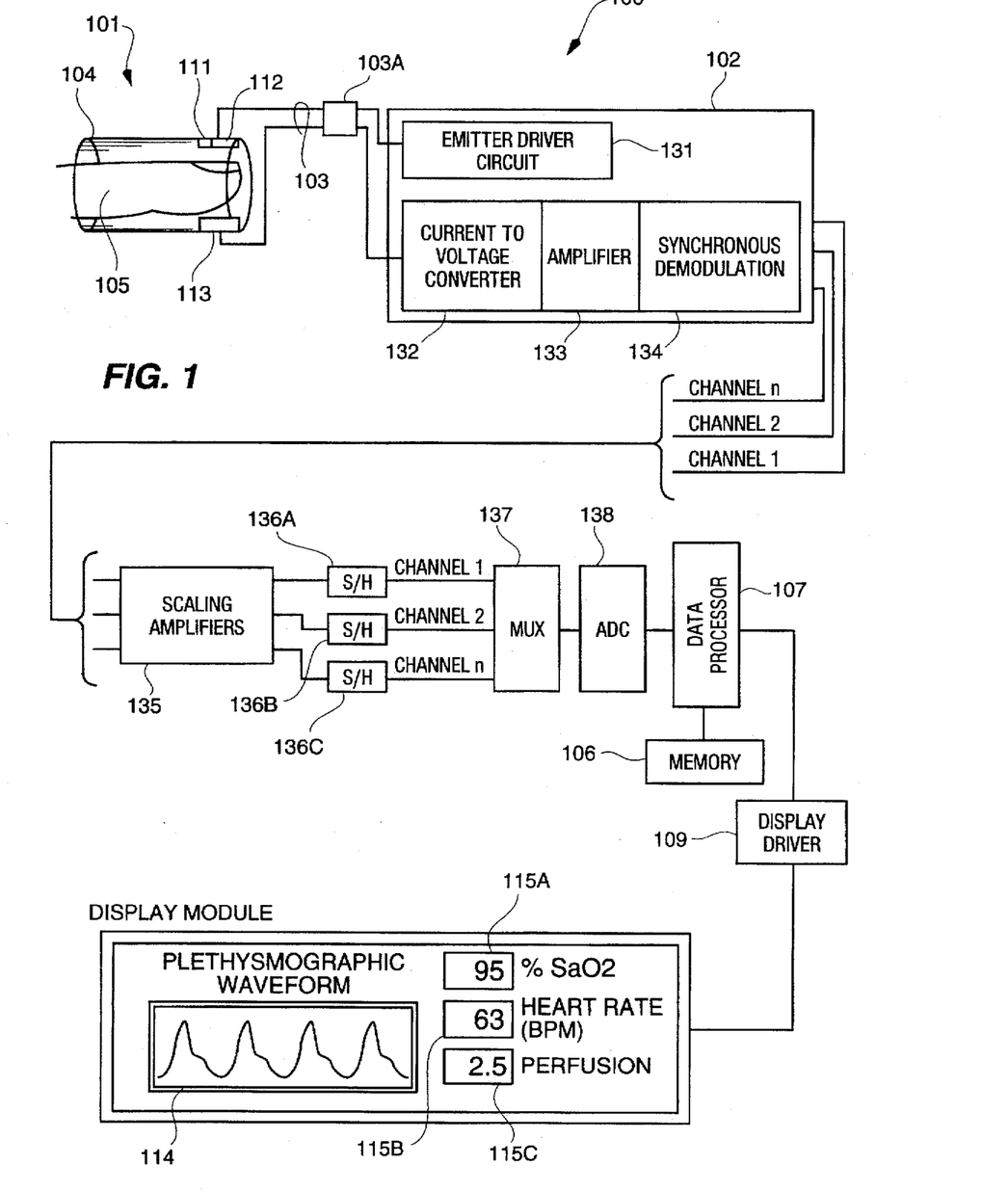
FIG. 1 illustrates in block diagram form the overall architecture of a typical photoplethysmographic instrument which includes the probe characterizing apparatus of the present invention.

Any improvements, however incremental, in the design, manufacturability and performance of a probe in the field of medical monitoring instruments represents a significant advance. FIG. 1 illustrates in block diagram form the elements that comprise a typical medical monitoring instrument. The medical monitoring apparatus primarily consists of two segments: an electronics (control) module, typically resident within the monitor housing, and a probe module that is affixed to a probe attachment site on the patient and connected to the control module via a cable. For the following description, the term "probe" is construed to include the light emitting and detector devices, apparatus used to affix the probe to a monitoring site on the patient, signal conductors and connectors used to couple the probe to the control module.

Photoplethysmographic Probe Application

To illustrate the operation of the apparatus of the present invention, its use in a pulse oximeter instrument application is described herein. A pulse oximeter instrument is frequently used to monitor the condition of a patient in a hospital or home setting. The pulse oximeter instrument noninvasively measures the oxygen saturation of the arterial blood and produces a human readable display that indicates the patient's heart rate, the oxygen saturation of the arterial blood, and optionally, the concentration of other hemoglobin species in the arterial blood. These readings are important to enable the medical staff to determine whether the patient's respiratory system is functioning properly, supplying sufficient oxygen to the blood.

A pulse oximeter instrument operates by use of a probe that applies radiation in the red and infrared wavelengths to a monitoring site on the patient (such as a finger, earlobe, or the nasal septum) that is rich in arterial blood and measures the differential change in the received intensity of light to thereby determine oxygen saturation of the arterial blood. The pulse oximeter instrument makes use of a plurality of light-emitting devices, each of which transmits light at a predetermined wavelength, which wavelengths are selected such that at least one is highly absorbed by oxygenated hemoglobin in the arterial blood and at least one is highly absorbed by reduced hemoglobin in the arterial blood. The differential change in absorption of the light beams generated by these light emitting devices by the selected hemoglobin species is a measure of the relative concentration of the hemoglobin species (oxygenated hemoglobin, reduced hemoglobin, carboxyhemoglobin and methemoglobin) contained in the arterial blood. The absorption of the light that is being transmitted through the monitoring site of the patient includes a constant portion that is a result of skin, bone, steady-state (venous) blood flow and light loss due to various other factors. The pulsatile component of absorption is due to the pulsatile arterial blood flow and is a small fraction of the received signal and is used by the pulse oximeter instrument to perform its measurements.

The measurements are computed by sampling the output of the light detector located in the probe to determine the incremental change in absorption of the various wavelengths of light transmitted through the monitoring site of the patient. These incremental changes in light absorption are then used to compute the oxygen saturation of the arterial blood as well as the patient's pulse rate. Since the pulsatile component of the signals received by the light detector represent only a small fraction of the incident light, it is important that the incident light be of significant magnitude to result in transmitted signals that have sufficient amplitude to provide accurate readings.

Probe Architecture

FIG. 1 illustrates in block diagram form the overall architecture of a typical pulse oximeter system including the apparatus of the present invention. The pulse oximeter system 100 consists of a probe 101 connected to probe interface circuit 102 by means of a set of signal conductors 103. The probe 101 consists of an exterior housing 104 that positions the active elements of the probe juxtaposed to the tissue under test, such as a finger 105, containing an arterial blood flow that is to be monitored. Included within housing 104 is a pair of light emitting diodes 111, 112 and at least one corresponding light detector 113. The light emitting diodes 111, 112 each produce an output light beam of predetermined wavelength which is directed at the tissue under test 105 enclosed by housing 104. The light detector 113 monitors the intensity of the light that is transmitted through or reflected from the vascularized tissue 105.

The signals received by probe interface circuit 102 from light detector 113 are analog signals representative of the intensity of the light received at light detector 113 and are typically processed by additional analog circuitry 132–137. The analog circuits comprise current to voltage converter 132 which translates the current signal output by detector 113 to a voltage, which is amplified by amplifier 133 and demodulated by demodulator 134 for processing on an individual channel basis by scaling amplifiers 135. Sample and hold circuits 136* receive individual channel signals which are multiplexed by multiplexer 137 and then converted by an analog-to-digital converter circuit 138 into sets of digital measurements which are stored in memory 106. Data processing circuit 107 mathematically processes the digitized measurements stored in memory 106 to compute the oxygenation level of the hemoglobin in the arterial blood in tissue 105. The data processing circuit 107 can also compute the pulse rate, and, optionally, the concentration of other hemoglobin species if more than two wavelengths of light are used. The results of the oxygen saturation computation and pulse rate are typically displayed numerically (115*) via display driver 109 and the associated display 115* while the plethysmographic waveform is typically displayed graphically via display 114. The perfusion measurement can be conveyed by numerical or graphical methods. The operation of data processing circuit 107 is disclosed in additional detail below and, for the purpose of this disclosure, it is assumed that the other elements disclosed in FIG. 1 are the conventional components found in existing pulse oximeter systems.

Probe Philosophy

Figure 6:
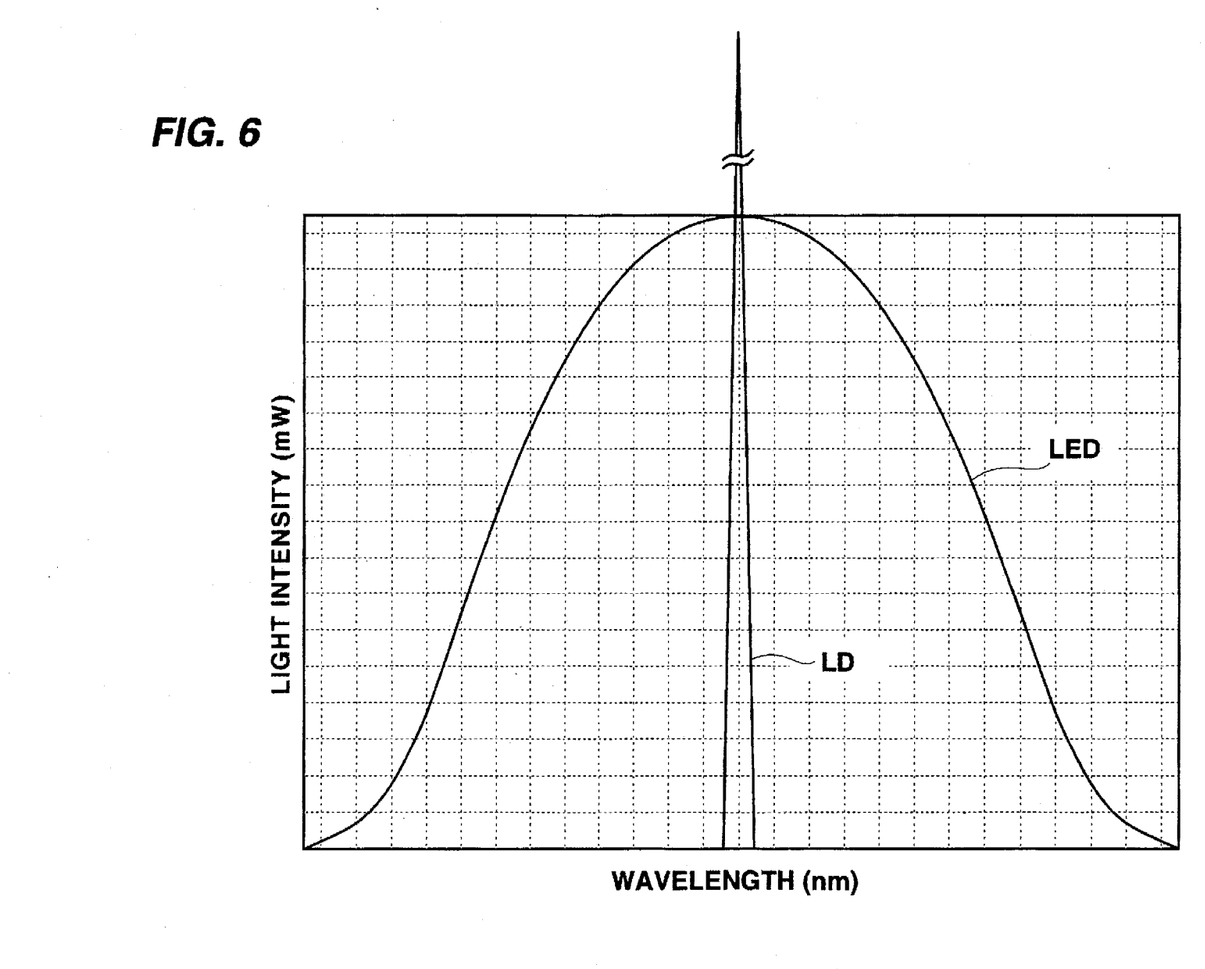

The light emitting devices used in the photoplethysmographic (pulse oximeter) instrument application disclosed herein are light emitting diodes. Each light emitting diode has a characteristic curve indicative of the intensity of the various wavelengths of light produced by the device. The probe also includes at least one light detector device, each light detector device having a characteristic curve indicative of the sensitivity of the light detector device to various wavelengths of light. FIG. 6 illustrates a typical curve that is indicative of the spectral output of the light emitting diodes, with the light emitting diode producing a beam of light, whose spectral output is centered about a selected wavelength, such as 660 nm, and having a typical bandwidth of 20 nm or greater. The shape of the spectral output curve can vary in extent as well as among the curve shapes of: bell shaped, asymmetrical, multiple peaks (notched). This variations in bandwidth and shape of the output characteristic curve among light emitting diodes affects the received signal and represents a significant problem.

Theory

The absorption of the optical signal by the selected hemoglobin species is computed by measuring differential changes in received light intensity as a function of changes in the path length, $L_P$, with the basic optical signal being described by an exponential relationship termed Beer's law. This means that the received signal intensity of Red, $I_{Red}$, and the intensity of the InfraRed, $I_{IR}$, light transmitted through the monitoring site on the patient and absorbed by the blood in a pulsing capillary bed can be described by the following equations:

$$I_{Red} = \text{Ambient} + I_{NPRed} * Exp[-\epsilon_{Red} * C * L_P] \qquad (1)$$

$$I_{IR} = \text{Ambient} + I_{NPIR} * Exp[-\epsilon_{IR} * C * L_P] \qquad (2)$$

where the Red or InfraRed optical absorption is given by the product of the Red Extinction Coefficient, $\epsilon_{Red}$, or InfraRed Extinction Coefficient, $\epsilon_{IR}$, the hemoglobin concentrations, C and the path length L. The concentration, C, and pulsatile path length, $L_P$, are the same for the Red and InfraRed wavelengths. $I_{NPRed}$ is the non-pulsatile red intensity of the signal and is proportional to the product of the light emitting diodes intensity with attenuation factors from propagation through non-pulsatile media and sensitivity and gain factors from the detection electronics. $I_{NPIR}$ is the corresponding non-pulsatile infrared intensity.

The pulsatile exponential function puts an amplitude modulation on the non-pulsatile intensity. The equation for the non-pulsatile intensity, $I_{NP}$, has several terms.

$$I_{NP} = Io * A * Exp[-\Sigma(\epsilon x * Cx * Lx)] \qquad (3)$$

The term Io is the incident intensity. A is a composite scale factor caused by scattering losses, losses in detection, and gain in detection circuits. There is a composite exponential absorption as the light propagates through non-pulsatile intervening tissue, which can be described by a summation of the absorptions by each intervening tissue zone.

In this system, a key parameter is called the RRatio. This parameter measures the ratio of the red arterial optical absorption to the infrared arterial optical absorption. The significance of the RRatio can be understood by examining the optical behavior of light as it passes through tissue. The light is scattered and absorbed by all the tissues, but the light passing through a pulsing artery or arterial bed sees a varying path length. The other tissues are unmoving and contribute to the steady non-pulsatile signal, but not to the time-varying pulsatile signals. The absorption of light by arterial blood is assumed to be only a function of the oxygenation state of the hemoglobin. Other basic requirements are that the red and infrared light travels along essentially the same optical path, and that all the hardware circuits do not introduce any bias into the signal extraction. The objective of the following mathematical manipulation is to obtain the ratio (RRatio) of the optical extinction coefficients of the Red and the InfraRed signals. This RRatio is used with a calibration equation to determine how well the blood is oxygenated. It is assumed that the ambient light (the term "Ambient" in equation 1) is perfectly subtracted from the received signals.

The extinction coefficients can be computed from the exponential factors of equations 1 and 2. This is typically done with the use of either logarithms or derivatives. The preferred method disclosed herein uses derivatives. If the samples are closely spaced relative to the changes in pulsatile path length, $L_P$, then a series expansion of the exponential function can be used. This means that the exponential really looks like a constant plus a term that is linearly proportional to the path length. In other words, only the first two terms of the binomial expansion need to be retained. Assume that the difference between two closely spaced in time non-pulsatile light intensities is zero. Taking samples at time t2 and time t1, the derivative of the red intensity can be approximated as the difference between the two samples:

$$
\begin{aligned}
DRed &= I_{NPRed}*(Exp[-\epsilon_{Red}*C*L_p(t_2)] - Exp[-\epsilon_{Red}*C*L_p(t_1)]) \approx \\
&I_{NPRed}*([1 - \epsilon_{Red}*C*L_p(t_2)] - [1 - \epsilon_{Red}*C*L_p(t_1)]) = \\
&I_{NPRed}*(\epsilon_{Red}*C*[L_p(t_2) - L_p(t_1)])
\end{aligned} \qquad (4)
$$

In equation 4, $L_P(t2)$ is the pulsatile path length at time 2 and $L_P(t1)$ is the pulsatile path length at time 1.

The derivative of the infrared intensity can be approximated in a similar manner.

$$DIR = I_{NPIR}*(\text{Exp}[-\epsilon_{IR}*C*L_p(t2)] - \text{Exp}[-\epsilon_{IR}*C*L_p(t1)]) \approx$$
$$I_{NPIR}*([1-\epsilon_{IR}*C*L_p(t2)] - [1-\epsilon_{IR}*C*L_p(t1)]) =$$
$$I_{NPIR}*(\epsilon_{IR}*C*[L_p(t2)-L_p(t_1)]) \quad (5)$$

Note that both DRed and DIR are directly proportional to the extinction coefficients $\epsilon$ as long as $I_{NPRed}$ and $I_{NPIR}$ are constant over that sampling interval. Note also that the term $C*[L_p(t2)-L_p(t1)]$ is common to both DRed and DIR. This means that the ratio of DRed and DIR is independent of the hemoglobin species concentration and changes in path length.

$$DRed/DIR=(I_{NPRed}/I_{NPIR})*(\epsilon_{Red}/\epsilon_{IR}) \quad (6)$$

Now the factor which is due to the ratio of received non-pulsatile intensities can be removed in several ways. In one method, analog hardware is used to separate the received intensities, by finding the low-pass DC values of the red and infrared signals.

$$(I_{NPRed}/I_{NPIR})=(I_{NPRed\,DC}/I_{NPIRDC}) \quad (7)$$

In the preferred method, the average of the two or more time samples is used $$I_{NPRed}=I_{NPRed(t2)}+I_{NPRed(t1)}+\ldots/N \quad (8)$$
$$I_{NPIR}=I_{NPIR(t2)}+I_{NPIR(t1)}+\ldots/N \quad (9)$$

An instantaneous RRatio is found by multiplying the ratio of derivatives to the ratio of the non-pulsatile intensities.

$$\text{instantaneous } RRatio=(\epsilon_{Red}/\epsilon_{IR})=(DRed/DIR)*(I_{NPIR}/I_{NPRed}) \quad (10)$$

Figure 8:
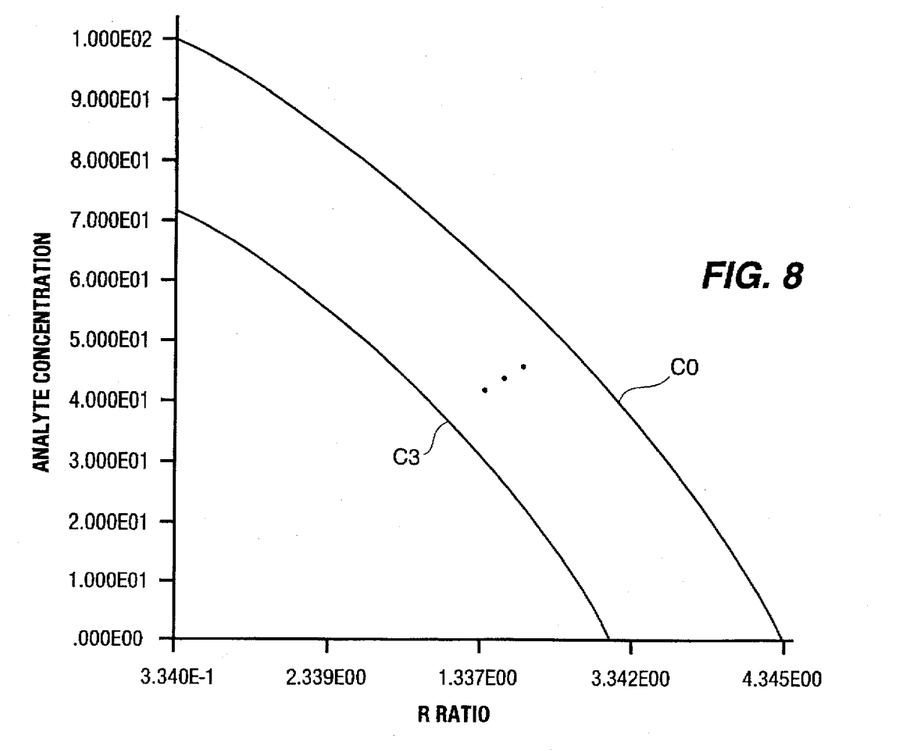
FIG. 8 illustrates a family of characteristic curves.

The resultant RRatio is then typically used with an empirically determined transfer curve, such as illustrated in FIG. 8, which is based on the calibration equation, to translate the measured received red and infrared light intensities to a value for oxygen concentration of the arterial blood. The use of a single empirically determined transfer curve presumes a fixed, known operating wavelength for the light emitting device and no additional effects introduced by the remaining optical characteristics of the probe system. As noted above, there are a number of additional factors that effect the accuracy of the resultant measurements.

Computation Process

Figure 2:
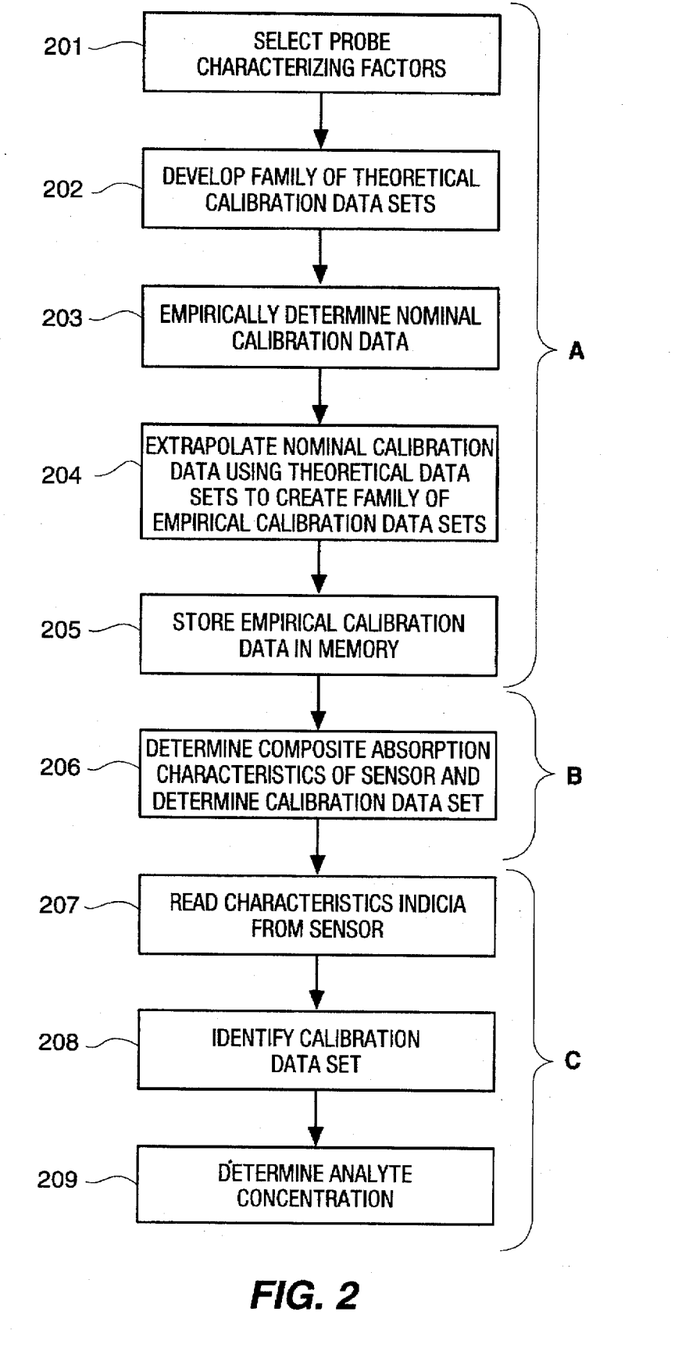
FIGS. 2–3 illustrate in flow diagram form the operational steps taken by apparatus to generate the transfer characteristic for the probe and use this information to program a monitor instrument.
Figure 3:
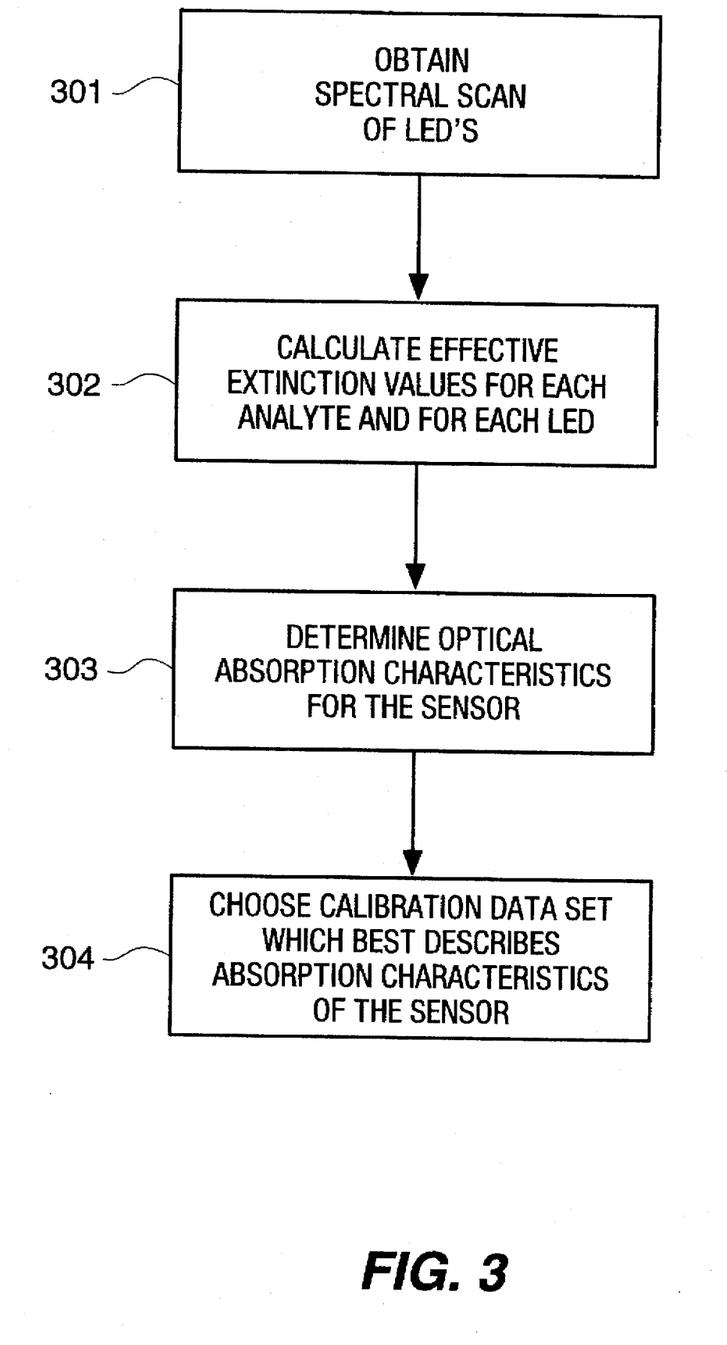

FIGS. 2 and 3 illustrate in flow diagram form the operational steps taken by a monitor probe composite indicia calculating device that is connected to the apparatus of the present invention to precisely determine the composite characteristics that are unique to a selected probe. The process is divided into three parts: A—compute basic family of calibration curves, B—measure probe characteristics, C—operate system with probe. The factors of the probe being considered are identified at step 201. The first portion of this process is to create a family of composite transfer characteristic curves. Each characteristic curve in the family of characteristic curves represents an interrelationship between a measured ratio of optical extinctions of a selected analyte at two selected wavelengths of light and a value for concentration of said selected analyte in said subject. In the specific embodiment described herein, the analyte is oxygen saturation of the subject's arterial blood, which is determined by measuring the absorptivity of oxygenated hemoglobin and reduced hemoglobin in the arterial blood at two selected wavelengths of light. It is known that the incremental differences among the individual, empirically determined characteristic curves in the family of characteristic curves is substantially identical to the theoretically computed variation among the individual characteristic curves. Therefore, one method of generating the family of composite characteristic curves is to at step 202 theoretically develop a family of compensation curves then empirically determine, at step 203 in well known fashion, the nominal calibration curve for the probe at a selected wavelength of light and then extrapolate at step 204 the calibration set of data that represents this curve into a family of curves as shown in FIG. 8 using the theoretical computations for a plurality of wavelengths. These operations are well known and are performed external to the apparatus of FIG. 1. The resultant family of curves are stored at step 205 in memory 106 to enable the system to compute the oxygen saturation of the arterial blood.

Figure 4:
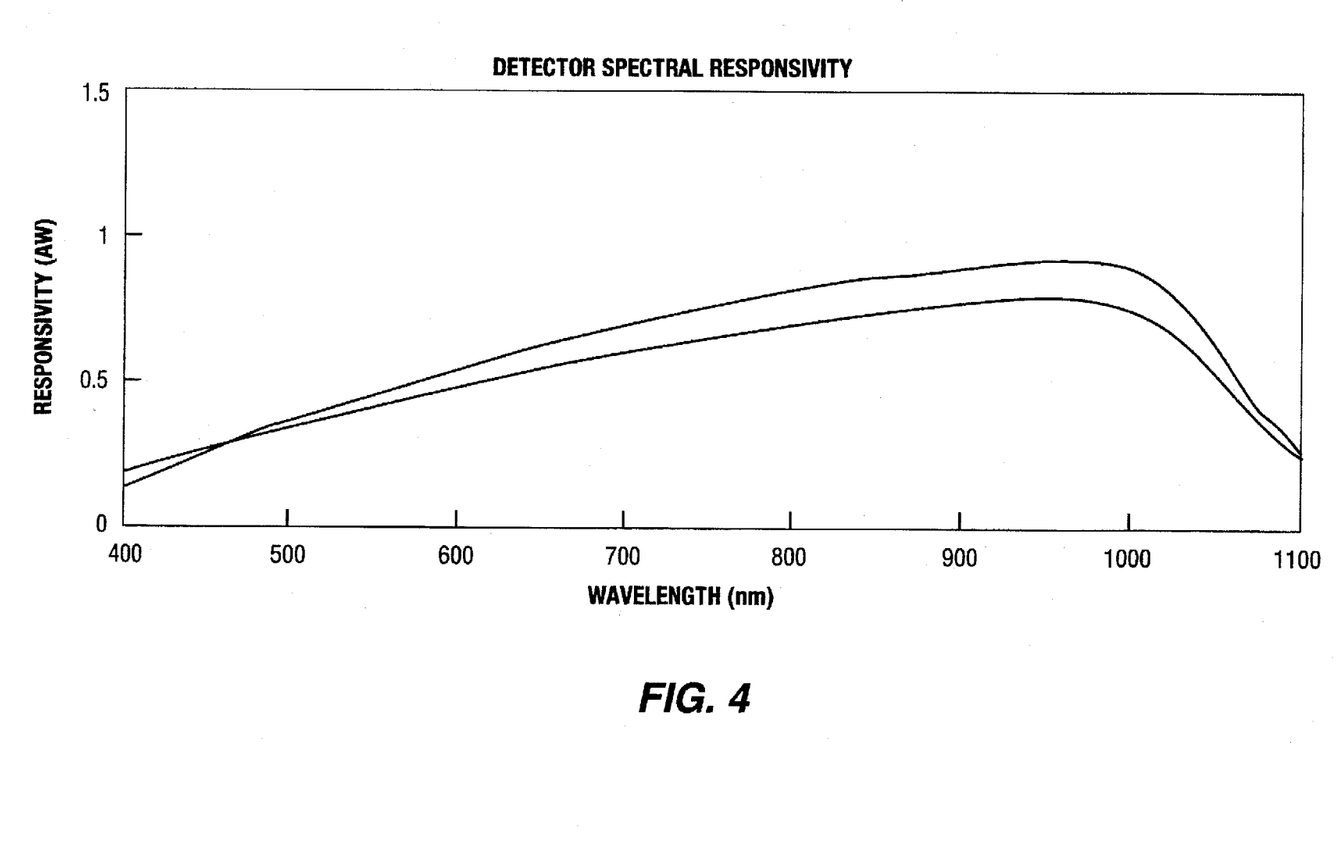
FIGS. 4–6 illustrate typical characteristic curves of light detector devices, extinction curve characteristics, and light emitting devices, respectively.
Figure 5:
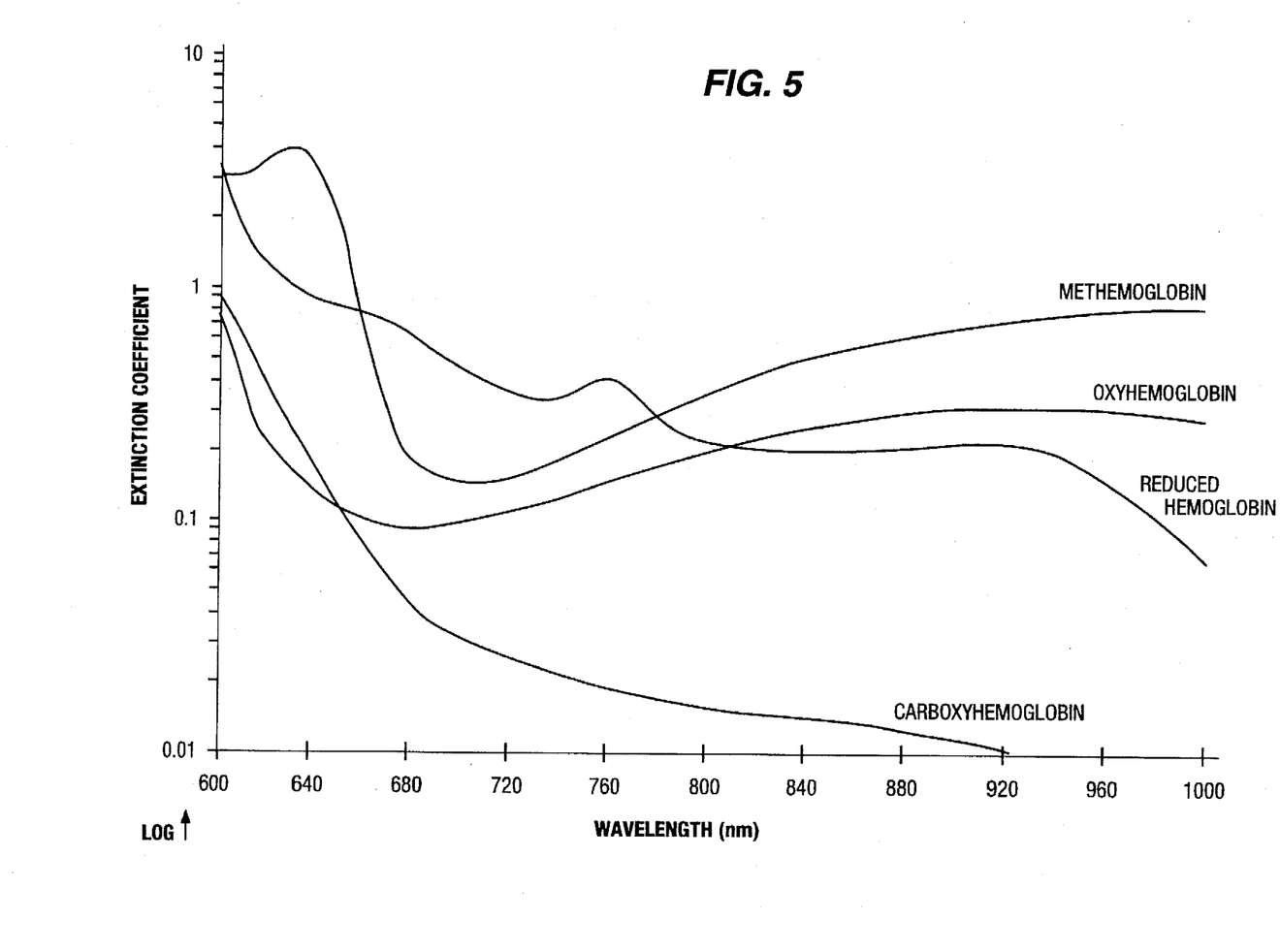

The method of selecting the one of the plurality of composite characteristic curves stored in memory 106 is by use of a composite probe characteristic. The composite probe characteristic is computed from a plurality of factors selected at step 201 from the group including: light emitting device nominal wavelength, light emitting device characteristic curve bandwidth, light emitting device characteristic curve waveshape, light emitting device characteristic curve centroid, light detector characteristic curve waveshape, light detector characteristic curve centroid, light detector device characteristic curve bandwidth, analyte extinction curves. The method for determining the composite transfer characteristic curve for the probe disclosed herein as the preferred embodiment involves overlaying the selected factors, which here comprise the light emitting device characteristic curves (FIG. 6), the light detector device characteristic curve (FIG. 4), and each extinction curve (FIG. 5) for the corresponding analyte of interest.

The programming apparatus (not shown) computes the dot product of these curves in step 206 and this value is then normalized by dividing out the relative intensity and sensitivity values of the light emitting device and detector curves. The resulting effective extinction value represents the interaction of the curves for a given analyte. A value can be obtained at step 206 by computing a weighted summation of these effective extinction values based on a single concentration of the analytes of interest. After characterizing the probe in this manner, a composite calibration value exists for each light emitting device in the probe. This composite characteristic value is programmed into the probe, so the probe is self-defining. The manner of programming the probe can be the traditional use of a binning resistor, mounted in the probe and readable at step 207 by the control module to identify which of the plurality of stored composite characteristic curves are appropriate to use for this probe.

The processing at step 206 is illustrated in FIG. 3 as follows:

Step 301: Obtain a spectral scan of the RED and IR LED for a given emitter assembly.

Step 302: Calculate effective extinction values for reduced hemoglobin RHB, oxygenated hemoglobin O2HB, carboxyhemoglobin COHB and methemoglobin MHB at both red RED and infrared IR wavelengths. Effective extinction is calculated by overlaying the spectral scan which is a function of emitter intensity and detector responsivity with each extinction curve, multiplying point by point, summing these values, and then normalizing by dividing out the sum of the spectral scan intensities. The equation of effective extinction is:

$$E\epsilon_{LED}^{hem} = \frac{\Sigma(LEDi*DETi*EXTi)}{\Sigma(LEDi*DETi)} \quad (11)$$

Step 303: The resultant effective extinction value for each hemoglobin species of interest is used to calculate optical absorption for each light emitting diode LED. For example, assume that the following concentrations of hemoglobins are present in the arterial blood: O2HB=95%, RHB=3%, COHB=1.5%, MetHB=0.5%. The optical absorption value for an LED at these concentrations is given by the following equation:

$$A_{LED1} = E\epsilon_{LED1}^{O2HB}*0.95 + E\epsilon_{LED1}^{RHB}*0.03 + E\epsilon_{LED1}^{COHB}*0.015 + E\epsilon_{LED1}^{MetHB}*0.005 \quad (12)$$

Step 304: Several methods can be used to correlate the resultant optical absorption values with calibration data to be used for calculating hemoglobin concentration. The method which allows for the greatest acceptance of component variation considers the ratios of optical absorption for the probe components at various hemoglobin concentration levels. This creates unique calibration data for a given probe. This calibration data for the given probe can be stored in memory located in the probe itself for use by the measurement system to calibrate the saturation levels or the probe calibration data can be compared to calibration data preprogrammed in memory 106 to determine which pre-existing data set best describes the optical absorption characteristics of that probe.

The ratio of optical absorption is given by the equation:

$$R = \frac{A_{LED1}}{A_{LED2}} = \quad (13)$$

$$\frac{E\epsilon_{LED1}^{O2HB}*O2HB + E\epsilon_{LED1}^{RHB}*RHB + E\epsilon_{LED1}^{COHB}*COHB + E\epsilon_{LED1}^{MetHB}*MetHB}{E\epsilon_{LED2}^{O2HB}*O2HB + E\epsilon_{LED2}^{RHB}*RHB + E\epsilon_{LED2}^{COHB}*COHB + E\epsilon_{LED2}^{MetHB}*MetHB}$$

The calibration data set for computing oxygen saturation is determined by setting the concentrations for COHB and MetHB to typical levels and varying the levels of O2HB and RHB.

Figure 7:
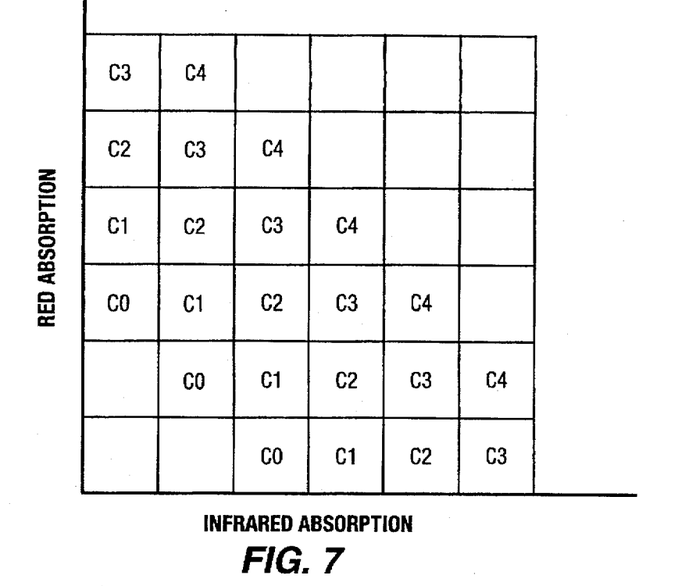
FIG. 7 illustrates a selection matrix used to translate the probe characterizing indicia to a selected characteristic curve in the family of characteristic curves.

In systems where the allowable number of calibration data sets is small or the variations among components is kept to a minimal number, a single R value for each probe is sufficient to identify the calibration data set which best describes the optical absorption characteristics of that probe. These systems have a one to one correlation between an R value at a given concentration and calibration data sets. As a system allows for increased variation among components, a single R value is no longer sufficient to uniquely identify the optical absorption characteristics of the probe. In these systems, an optical absorption value at a given concentration for each LED may suffice in identifying the best calibration data set. This relationship between the computed optical absorptions and the characteristic curve is determined using a correspondence matrix at step 208. The correspondence matrix is illustrated in FIG. 7 wherein along one axis (vertical) is charted the values of the determined red absorption while along the other orthogonal axis (horizontal) is charted the determined infrared absorption. The intersection of a particular set of values for this graph resides in a one of a plurality of predefined regions (squares), each of which is labeled to indicate an identified one of the plurality of curves in the family of curves that should be used to compute the SpO2 from the measured value of RRatio. In systems which allow for the greatest acceptance of component variations, the probe's unique calibration data set is computed by determining the R values at various concentration levels and used to identify the calibration data to be used by the measurement system as previously described.

The processor 107 selects the value identified from the correspondence matrix at step 208 and uses this data to identify a curve at step 208 from the calibration set stored in memory 106. The calibration values determined at step 206 are used as shown in FIG. 7 to assign calibration data to that probe from an existing set of calibration data. In a probe that has two light emitting devices, one method of making this assignment is to look at the ratio of the optical absorption values for the two light emitting devices at various concentration levels. This results in a calibration curve that is specific to that probe. The specific curve can then be matched against the existing family of composite characteristic curves (FIG. 8) in the calibration data set to find the existing prestored characteristic curve that best describes the probe.

The medical monitoring apparatus makes use of the stored calibration data and the determined probe composite characteristic value by determining at step 207 the impedance value of the binning resistor located in the probe when the instrument is turned on. This determined binning resistor value then indicates at step 208 which of the selected composite characteristic curves is to be used in reading data from the memory. Thus, if the binning resistor is of a value C2, and the control module determines from the correspondence matrix that curve 2 is to be used, the processor reads at step 209 calibration data values from the memory that correspond to the second composite curve stored therein when performing the table look-up process to determine at step 209 the value of oxygen saturation from the computed value of the RRatio.

SUMMARY

Thus, this system not only identifies the present value of a plurality of operating characteristics of the optical components contained in the probe, but also computes the interrelationship therebetween to produce a characterizing indicia that substantially defines the net operating characteristics of the probe, including the interrelation of the various interactive and/or cumulative effects. This indicia represents a composite number that can be used directly by the processor contained within the photoplethysmographic apparatus to perform the required computations. This process produces a system that has increased accuracy and allows for greater variation among probe components.

I claim:

1. A method of compensating for variations in operating characteristics of a probe in the determination of analyte concentration, which probe contains a plurality of light emitting devices, each light emitting device having a characteristic curve indicative of the intensity of the various wavelengths of light produced by the device, and at least one light detector device, each light detector device having a characteristic curve indicative of the sensitivity of the light detector device to various wavelengths of light, said probe being operative to measure, via optical extinction at a monitoring site on a subject, a concentration of analytes contained in said subject to which said probe is connected, comprising the steps of:

storing in a memory, calibration data sets which define an interrelationship between a measured ratio of optical extinctions of a selected analyte at two selected wavelengths of light and a value for concentration of said selected analyte in said subject;

identifying a determined composite probe characteristic indicative of optical performance of said probe at a plurality of wavelengths, said composite probe characteristic being computed from a plurality of factors selected from the group consisting of: light emitting device nominal wavelength, light emitting device characteristic curve bandwidth, light emitting device characteristic curve waveshape, light emitting device characteristic curve centroid, light detector characteristic curve waveshape, light detector characteristic curve centroid, light detector device characteristic curve bandwidth; and computing, in response to a measured intensity of light at said monitoring site, a concentration of said selected analyte in said subject using said composite probe characteristic and corresponding calibration data set.

2. The method of claim 1 wherein said composite probe characteristic is computed by taking a dot product of said selected factors over a range of wavelengths.

3. The method of claim 2 further comprising the step of:
storing data in said probe indicative of said computed composite probe characteristic.

4. The method of claim 3 wherein said memory stores data indicative of a family of calibration data sets, said step of identifying comprises:

reading said data, indicative of said assigned composite probe characteristic, from said probe; and identifying a one of said family of calibration data sets corresponding to said assigned composite probe characteristic.

5. The method of claim 4 wherein said step of computing comprises:

receiving data indicative of a measured optical extinction at each of said two selected wavelengths of light; and using said received data indicative of measured optical extinction to retrieve a value for concentration of said selected analyte in said subject from said identified calibration data set.

6. The method of claim 3 wherein said data indicative of said computed composite probe characteristic comprises a single data value indicative of an effective optical extinction for said probe.

7. The method of claim 3 wherein said data indicative of said computed composite probe characteristic comprises an impedance of an element mounted in said probe.

8. The method of claim 2 further comprising the step of:
storing data in said probe indicative of a unique calibration data set corresponding to said assigned composite probe characteristic.

9. The method of claim 8 further comprising the step of:
reading said stored data, indicative of said unique calibration data set corresponding to said assigned composite probe characteristic into said memory for use by said step of computing.

10. Apparatus for compensating for variations in operating characteristics of a probe in the determination of analyte concentration, which probe contains a plurality of light emitting devices, each light emitting device having a characteristic curve indicative of the intensity of the various wavelengths of light produced by the device, and at least one light detector device, each light detector device having a characteristic curve indicative of the sensitivity of the light detector device to various wavelengths of light, said probe being operative to measure, via optical extinction at a monitoring site on a subject, a concentration of analytes contained in said subject to which said probe is connected, comprising:

a memory for storing data indicative of at least one calibration data set, which defines an interrelationship between a measured ratio of optical extinctions of a selected analyte at two selected wavelengths of light and a value for concentration of said selected analyte in said subject;

means for identifying a determined composite probe characteristic indicative of optical performance of said probe at a plurality of wavelengths, said composite probe characteristic being computed from a plurality of factors selected from the group consisting of: light emitting device nominal wavelength, light emitting device characteristic curve bandwidth, light emitting device characteristic curve waveshape, light emitting device characteristic curve centroid, light detector characteristic curve waveshape, light detector characteristic curve centroid, light detector device characteristic curve bandwidth; and means, responsive to a measured intensity of light at said monitoring site, for computing a concentration of said selected analyte in said subject using said at least one calibration data set and said composite probe characteristic.

11. The apparatus of claim 10 wherein said composite probe characteristic is computed by taking a dot product of said selected factors over a range of wavelengths.

12. The apparatus of claim 11 further comprising:
means for storing data in said probe indicative of said computed composite probe characteristic.

13. The apparatus of claim 12 wherein said memory stores data indicative of a family of calibration data sets, said identifying means comprises:

means for reading said data, indicative of said assigned composite probe characteristic, from said probe; and means for identifying a one of said family of calibration data sets corresponding to said assigned composite probe characteristic.

14. The apparatus of claim 13 wherein said computing means comprises:

means for receiving data indicative of a measured optical extinction at each of said two selected wavelengths of light; and means for using said received data indicative of measured optical extinction to retrieve a value for concentration of said selected analyte in said subject from said identified calibration data set.

15. The apparatus of claim 12 wherein said data indicative of said computed composite probe characteristic comprises a single data value indicative of an effective optical extinction for said probe.

16. The apparatus of claim 12 further comprising:
coding means mounted in said probe, an impedance of which comprises said data indicative of said computed composite probe characteristic.

17. The apparatus of claim 12 further comprising:
means for storing data in said probe indicative of a unique calibration data set corresponding to said assigned composite probe characteristic.

18. The apparatus of claim 17 further comprising:
means for reading said stored data, indicative of said unique calibration data set corresponding to said assigned composite probe characteristic into said memory for use by said computing means.

* * * * *